US009512484B2

(12) United States Patent
Pendino et al.

(10) Patent No.: US 9,512,484 B2
(45) Date of Patent: Dec. 6, 2016

(54) METHODS FOR DETERMINING A PROGNOSIS FOR SURVIVAL FOR A PATIENT WITH BREAST CANCER

(75) Inventors: Frederic Pendino, Bagneux (FR); Johan R. Lillehaug, Bergen (NO); Thomas Aloysius, Loddefjord (NO); Stian Knappskog, Bergen (NO)

(73) Assignee: Bergen Teknologioverforing AS, Bergen (NO)

( * ) Notice: Subject to any disclaimer, the term of this patent is extended or adjusted under 35 U.S.C. 154(b) by 850 days.

(21) Appl. No.: 13/145,859

(22) PCT Filed: Dec. 8, 2009

(86) PCT No.: PCT/NO2009/000423
§ 371 (c)(1),
(2), (4) Date: Sep. 28, 2011

(87) PCT Pub. No.: WO2010/085153
PCT Pub. Date: Jul. 29, 2010

(65) Prior Publication Data
US 2012/0021927 A1    Jan. 26, 2012

(30) Foreign Application Priority Data

Jan. 23, 2009  (NO) ................................. 20090358
Jun. 9, 2009   (WO) ................ PCT/NO2009/000214

(51) Int. Cl.
*C12Q 1/68*    (2006.01)

(52) U.S. Cl.
CPC ....... *C12Q 1/6886* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

2011/0145176 A1*   6/2011  Perou et al. .................... 706/12

* cited by examiner

*Primary Examiner* — Catherine S Hibbert
(74) *Attorney, Agent, or Firm* — Whitham, Curtis & Cook, P.C.

(57) ABSTRACT

A method for determining a prognosis for survival for a patient with breast cancer is described. Also described is a method for monitoring the effectiveness of a course of treatment for a patient with breast cancer, and the use of such a method in a kit. A kit determining the level of RINF is also described.

14 Claims, 2 Drawing Sheets

SEQUENCE LISTING

```
<160> NUMBER OF SEQ ID NOS: 9

<210> SEQ ID NO 1
<211> LENGTH: 1338
<212> TYPE: DNA
<213> ORGANISM: Homo sapiens

<400> SEQUENCE: 1
acccaggcct cttcattatg accccggcag gtgtgttcct ggccgagagc gcgctgcaca      60
tggcgggcct ggctgagtac cccatgcagg gagagctggc ctctgccatc agctccggca     120
agaagaagcg gaaacgctgc ggcatgtgcg cgccctgccg gcggcgcatc aactgcgagc     180
agtgcagcag ttgtaggaat cgaaagactg gccatcagat ttgcaaattc agaaaatgtg     240
aggaactcaa aaagaagcct tccgctgctc tggagaaggt gatgcttccg acgggagccg     300
ccttccggtg gtttcagtga cggcggcgga acccaaagct gccctctccg tgcaatgtca     360
ctgctcgtgt ggtctccagc aagggattcg ggcgaagaca aacggatgca cccgtcttta     420
gaaccaaaaa tattctctca cagatttcat tcctgttttt atatatatat tttttgttgt     480
```

```
cgttttaaca tctccacgtc cctagcataa aaagaaaaag aaaaaaattt aaactgcttt      540
ttcggaagaa caacaacaaa aaagaggtaa agacgaatct ataaagtacc gagacttcct      600
gggcaaagaa tggacaatca gtttccttcc tgtgtcgatg tcgatgttgt ctgtgcagga      660
gatgcagttt ttgtgtagag aatgtaaatt ttctgtaacc ttttgaaatc tagttactaa      720
taagcactac tgtaatttag cacagtttaa ctccaccctc atttaaactt cctttgattc      780
tttccgacca tgaaatagtg catagtttgc ctggagaatc cactcacgtt cataaagaga      840
atgttgatgg cgccgtgtag aagccgctct gtatccatcc acgcgtgcag agctgccagc      900
agggagctca cagaagggga gggagcacca ggccagctga gctgcaccca cagtcccgag      960
actgggatcc cccaccccaa cagtgatttt ggaaaaaaaa atgaaagttc tgttcgttta     1020
tccattgcga tctggggagc cccatctcga tatttccaat cctggctact tttcttagag     1080
aaaataagtc cttttttttct ggccttgcta atggcaacag aagaaagggc ttctttgcgt     1140
ggtcccctgc tggtgggggt gggtcccag ggggccccct gcggcctggg ccccctgcc      1200 cacgccagc ttcctgctga tgaacatgct gtttgtattg ttttaggaaa ccaggctgtt     1260
ttgtgaataa aacgaatgca tgtttgtgtc acgaaaaaaa aaaaaaaaaa aaaaaaaaa     1320 aaaaaaaaaa aaaaaaaa                                                  1338

<210> SEQ ID NO 2
<211> LENGTH: 969
<212> TYPE: DNA
<213> ORGANISM: Homo sapiens

<400> SEQUENCE: 2
atgtcgagcc tcggcggtgg ctcccaggat gccggcggca gtagcagcag cagcaccaat       60
ggcagcggtg gcagtggcag cagtggccca aaggcaggag cagcagacaa gagtgcagtg      120
gtggctgccg ccgcaccagc ctcagtggca gatgacacac caccccccga gcgtcggaac      180
aagagcggta tcatcagtga gcccctcaac aagagcctgc gccgctcccg cccgctctcc      240
cactactctt cttttggcag cagtggtggt agtggcggtg gcagcatgat gggcggagag      300
tctgctgaca aggccactgc ggctgcagcc gctgcctccc tgttggccaa tgggcatgac      360
ctggcggcgg ccatggcggt ggacaaaagc aaccctacct caaagcacaa agtggtgct       420 gtggccagcc tgctgagcaa ggcagagcgg gccacggagc tggcagccga gggacagctg      480
acgctgcagc agtttgcgca gtccacagag atgctgaagc gcgtggtgca ggagcatctc      540
ccgctgatga gcgaggcggg tgctggcctg cctgacatgg aggctgtggc aggtgccgaa      600
gccctcaatg gccagtccga cttcccctac ctgggcgctt tccccatcaa cccaggcctc      660
ttcattatga ccccggcagg tgtgttcctg gccgagagcg cgctgcacat ggcgggcctg      720
gctgagtacc ccatgcaggg agagctggcc tctgccatca gctccggcaa gaagaagcgg      780
aaacgctgcg gcatgtgcgc gccctgccgg cggcgcatca actgcgagca gtgcagcagt      840
tgtaggaatc gaaagactgg ccatcagatt tgcaaattca gaaaatgtga ggaactcaaa      900
aagaagcctt ccgctgctct ggagaaggtg atgcttccga cgggagccgc cttccggtgg      960
tttcagtga                                                              969

<210> SEQ ID NO 3
<211> LENGTH: 322
<212> TYPE: PRT
<213> ORGANISM: Homo sapiens

<400> SEQUENCE: 3
```

```
Met Ser Ser Leu Gly Gly Ser Gln Asp Ala Gly Ser Ser Ser
1               5                   10                  15

Ser Ser Thr Asn Gly Ser Gly Gly Ser Gly Ser Ser Gly Pro Lys Ala
            20                  25                  30

Gly Ala Ala Asp Lys Ser Ala Val Val Ala Ala Ala Pro Ala Ser
            35                  40                  45

Val Ala Asp Asp Thr Pro Pro Pro Glu Arg Arg Asn Lys Ser Gly Ile
50                      55                  60

Ile Ser Glu Pro Leu Asn Lys Ser Leu Arg Arg Ser Arg Pro Leu Ser
65                  70                  75                  80

His Tyr Ser Ser Phe Gly Ser Ser Gly Gly Ser Gly Gly Gly Ser Met
                85                  90                  95

Met Gly Gly Glu Ser Ala Asp Lys Ala Thr Ala Ala Ala Ala Ala
                100                 105                 110

Ser Leu Leu Ala Asn Gly His Asp Leu Ala Ala Met Ala Val Asp
        115                 120                 125

Lys Ser Asn Pro Thr Ser Lys His Lys Ser Gly Ala Val Ala Ser Leu
130                 135                 140

Leu Ser Lys Ala Glu Arg Ala Thr Glu Leu Ala Ala Glu Gly Gln Leu
145                 150                 155                 160

Thr Leu Gln Gln Phe Ala Gln Ser Thr Glu Met Leu Lys Arg Val Val
                165                 170                 175

Gln Glu His Leu Pro Leu Met Ser Gly Ala Gly Ala Gly Leu Pro Asp
                180                 185                 190

Met Glu Ala Val Ala Gly Ala Glu Ala Leu Asn Gly Gln Ser Asp Phe
                195                 200                 205

Pro Tyr Leu Gly Ala Phe Pro Ile Asn Pro Gly Leu Phe Ile Met Thr
210                 215                 220

Pro Ala Gly Val Phe Leu Ala Glu Ser Ala Leu His Met Ala Gly Leu
225                 230                 235                 240

Ala Glu Tyr Pro Met Gln Gly Glu Leu Ala Ser Ala Ile Ser Ser Gly
                245                 250                 255

Lys Lys Lys Arg Lys Arg Cys Gly Met Cys Ala Pro Cys Arg Arg Arg
                260                 265                 270

Ile Asn Cys Glu Gln Cys Ser Ser Cys Arg Asn Arg Lys Thr Gly His
                275                 280                 285

Gln Ile Cys Lys Phe Arg Lys Cys Glu Glu Leu Lys Lys Lys Pro Ser
                290                 295                 300

Ala Ala Leu Glu Lys Val Met Leu Pro Thr Gly Ala Ala Phe Arg Trp
305                 310                 315                 320

Phe Gln

<210> SEQ ID NO 4
<211> LENGTH: 18
<212> TYPE: DNA
<213> ORGANISM: Artificial Sequence
<220> FEATURE:
<223> OTHER INFORMATION: Synthetic oligonucleotide primer

<400> SEQUENCE: 4
tccgctgctc tggagaag                                              18

<210> SEQ ID NO 5
<211> LENGTH: 20
<212> TYPE: DNA
```

```
<213> ORGANISM: Artificial Sequence
<220> FEATURE:
<223> OTHER INFORMATION: Synthetic oligonucleotide primer

<400> SEQUENCE: 5
cacacgagca gtgacattgc                                                20

<210> SEQ ID NO 6
<211> LENGTH: 15
<212> TYPE: DNA
<213> ORGANISM: Artificial Sequence
<220> FEATURE:
<223> OTHER INFORMATION: Synthetic oligonucleotide primer

<400> SEQUENCE: 6
atgcgctacg tcgcc                                                     15

<210> SEQ ID NO 7
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 7
ttaatcaaaa aggccaaatc ccat                                           24

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 8
aacccaaagc tgccctctcc                                                20

<210> SEQ ID NO 9
<211> LENGTH: 29
<212> TYPE: DNA
<213> ORGANISM: Artificial Sequence
<220> FEATURE:
<223> OTHER INFORMATION: Synthetic oligonucleotide primer

<400> SEQUENCE: 9
agctgaatgg aaaaaacatt gaagacgtc                                      29
```

METHODS FOR DETERMINING A PROGNOSIS FOR SURVIVAL FOR A PATIENT WITH BREAST CANCER

FIELD OF THE INVENTION

The present invention relates to a method for determining a prognosis for survival for a patient with breast cancer, and a method for monitoring the effectiveness of a course of treatment for a patient with breast cancer, and a kit for determining a prognosis for survival for a patient with breast cancer by quantifying the RINF mRNA expression.

BACKGROUND FOR THE INVENTION

Identification of genes specifically deregulated in tumour cells could bring to light new tumour suppressors and oncogenes with potential clinical applications in diagnostics, prognostics, and therapeutics. In Applicant's co-pending PCT application PCT/NO09/000214 we describe a new target gene of retinoids, CXXC5, encoding a nuclear factor that we have functionally characterized for the first time and named RINF (Retinoid-Inducible Nuclear Factor).

Our data indicated that RINF plays an essential role during in vitro human hematopoiesis. Indeed, expression studies and gene silencing experiments both demonstrate RINF implication during terminal differentiation of myeloid leukemia cells (NB4 and HL60 cell lines), but also during myelopoiesis of normal hematopoietic progenitors (bone marrow CD34+ cells). In keeping with its essential role during terminal myeloid differentiation and its localization to chromosome 5q31.3, a region often deleted in myeloid leukaemia (acute myeloid leukaemia and myelodysplasia), we have also suggested RINF as a promising tumor suppressor candidate at that locus in some myeloid malignancies.

Because RINF expression is not restricted to the hematopoietic tissue and may also be involved in development and/or homeostasis of other tissues, we have investigated RINF expression in some solid tumours derived from different tissues.

We have shown in Applicant's co-pending PCT application PCT/NO09/000214 that this gene could have a deregulated expression in some malignant tissues compared to their normal tissues of origin. Indeed, RINF mRNA expression was examined in solid tumour samples from patients suffering from breast cancer, and RINF expression was significantly higher in breast tumours compared to normal breast tissues controls.

SUMMARY OF THE INVENTION

We have now surprisingly found that the level of RINF expression correlates with the survival of patients with breast cancer.

The present invention thus relates to methods for determining the prognosis for survival, and for testing the effect of treatment regimens. The invention also relate to a kit for determining the prognosis for survival, and for testing the effect of treatment regimens.

DETAILED DESCRIPTION OF THE INVENTION

A first aspect of the present invention relates to a method for determining a prognosis for survival for a patient with breast cancer, wherein said method comprising:

(a) determining a measure for the level of RINF expression in a biological sample from said patient, (b) comparing the level of RINF expression in said sample to a reference level of RINF, wherein a level of RINF expression lower than the reference level in said sample correlates with increased survival of said patient, and wherein a level of RINF expression higher than the reference level in said sample correlates with decreased survival.

A preferred embodiment, said biological sample is a tumor, or a tumor biopsy or neoplastic cell containing sample.

In a preferred embodiment said measure for the level of RINF expression is determined by quantification of the expression of mRNA which encodes for a RINF protein, or a quantification of a nucleic acid comprising the sequence of SEQ ID NO1 or SEQ ID NO 2, or a functional fragment or variant thereof, or a functionally equivalent isolated DNA sequence hybridizable thereto.

In a further preferred embodiment is the level of RINF expression relative to said reference level used to determine a proper course of treatment for said patient.

In a preferred embodiment is the level of RINF expression determined by quantitative RT-PCR. More preferable, said quantitative RT-PCR uses Hydrolysis Probes targeting SEQ ID NO 1 or SEQ ID NO 2 for determining the RINF expression, and more preferable said RT-PCR uses primers amplifying exon 3 and 4, or exon 1 and 2 of SEQ ID NO 3.

Preferable, the level of RINF expression is determined based on the relative expression of RINF normalized to the expression of the rpP2 gene.

Preferable, the primers for the detection of SEQ ID NO 1 or 2 are

```
                                       (SEQ ID NO 4)
    5'-tccgctgctctggagaag-3', (SEQ ID NO 5)
    5'-cacacgagcagtgacattgc-3'
    and (SEQ ID NO 8)
    6-FAM-aacccaaagctgccctctcc-BBQ.
```

Preferable, the primers for the detection of rpP2 are

```
                                       (SEQ ID NO 6)
    5'-atgcgctacgtcgcc-3', (SEQ ID NO 7)
    5'-ttaatcaaaaaggccaaatcccat-3'
    and (SEQ ID NO 9)
    Cy5-agctgaatggaaaaaacattgaagacgtc-BBQ.
```

Preferable, the PCR amplification is conducted by an initial denaturation at 95° C. for 5 min, and than the samples is run through 44 cycles of the following conditions: denaturation for 10 seconds at 95° C. and elongation at 55° C. for 20 seconds.

In a further embodiment is the level of RINF expression determined immunochemically based on an antibody. Said antibody can be a polyclonal antibody, and is more preferable a monoclonal antibody. Preferable, said antibody is interacting with an epitope of a protein or protein sequence of SEQ ID NO 3, and more preferable said antibody is interacting with the amino acids 45-48 of SEQ ID NO 3.

In a further embodiment, the RINF expression is measured by a DNA, RNA or protein array.

In a further embodiment, said method further comprises a step (c);

(c) classifying said patient as belonging to either a first or a second group of patients, wherein said first group of patients having levels of RINF expression lower than the reference level is classified as having an increased likelihood of survival compared to said second group of patients having levels of RINF expression higher than the reference level.

In a further embodiment, said method further comprises a step (c);

(c) classifying said patient as belonging to either a first or a second group of patients, wherein said first group of patients having levels of RINF expression lower than said second group of patients, and where the first group of patients is classified as having an increased likelihood of survival compared to said second group of patients.

A second aspect of the present invention relates to a method for monitoring the effectiveness of a course of treatment for a patient with breast cancer, wherein said method comprising:

(a) determining a level of RINF expression in a biological sample from said patient prior to treatment, and (b) determining the level of RINF expression in a neoplastic cell-containing sample from said patient after treatment, whereby comparison of the level of RINF expression prior to treatment with the level of RINF expression after treatment indicates the effectiveness of said treatment, wherein a decrease in the level of RINF expression after treatment indicates that treatment is effective against said breast cancer.

A third aspect of the present invention relates to a use in accordance with any of the method claims, wherein at least one detection member for RINF is used in a kit for determining a prognosis for survival for a patient with breast cancer.

A forth aspect of the present invention relates to a kit for determining a prognosis for survival for a patient with breast cancer, characterized in that said kit comprises compounds capable of detecting the level of RINF expression in a biological sample.

Preferable embodiments for the second, third and forth aspects (independently for each aspect) are indicated below:
- said biological sample is a tumor, or a tumor biopsy or neoplastic cell containing sample.
- said measure for the level of RINF expression is determined by quantification the expression of mRNA which encodes for a RINF protein, or a quantification of a nucleic acid comprising the sequence of SEQ ID NO1 or SEQ ID NO 2, or a functional fragment or variant thereof, or a functionally equivalent isolated DNA sequence hybridizable thereto.
- the level of RINF expression relative to said reference level is used to determine a proper course of treatment for said patient.
- the level of RINF expression is determined by quantitative RT-PCR. More preferable, said quantitative RT-PCR uses Hydrolysis Probes targeting SEQ ID NO 1 or SEQ ID NO 2 for determining the RINF expression, and more preferable said RT-PCR uses primers amplifying exon 3 and 4, or exon 1 and 2 of SEQ ID NO 3.
- the level of RINF expression is determined based on the relative expression of RINF normalized to the expression of the rpP2 gene.
- the primers for the detection of SEQ ID NO 1 or 2 are

```
                                          (SEQ ID NO 4)
     5'-tccgctgctctggagaag-3', (SEQ ID NO 5)
     5'-cacacgagcagtgacattgc-3'
     and (SEQ ID NO 8)
     6-FAM-aacccaaagctgccctctcc-BBQ.
``` the primers for the detection of rpP2 are

```
                                          (SEQ ID NO 6)
     5'-atgcgctacgtcgcc-3', (SEQ ID NO 7)
     5'-ttaatcaaaaaggccaaatcccat-3'
     and (SEQ ID NO 9)
     Cy5-agctgaatggaaaaaacattgaagacgtc-BBQ.
```

- the PCR amplification is conducted by an initial denaturation at 95° C. for 5 min, and than the samples is run through 44 cycles of the following conditions: denaturation for 10 seconds at 95° C. and elongation at 55° C. for 20 seconds.
- the level of RINF expression is determined immunochemically based on an antibody. Said antibody can be a polyclonal antibody, and is more preferable a monoclonal antibody. Preferable, said antibody is interacting with an epitope of a protein or protein sequence of SEQ ID NO 3, and more preferable said antibody is interacting with the amino acids 45-48 of SEQ ID NO 3.
- the RINF expression is measured by a DNA, RNA or protein array.

DEFINITIONS

Prognosis is a medical term to describe the likely outcome of an illness. Here, a good "prognosis for survival" correlate with high rate survival of the patients and "bad prognosis for survival" correlate with a low rate of survival of the patient group.

EXPERIMENTAL SECTION

Materials and Methods
Quantitative RT-PCR of RINF

First-strand cDNA synthesis (RT) was carried out starting with total RNA (1 μg) in a 20 μl volume using oligo-dT primers with Transcriptor Reverse Transcriptase (Roche, Cat. N° 05 531 287 001) in accordance with the manufacturer's instructions. Quantitative PCRs were performed using specific Hydrolysis Probes targedting the CXXC5 gene on a Light Cycler 480 machine (Roche) in accordance with the manufacturer's instructions of the kit Lightcycler® 480 ProbesMaster (Cat. N° 04 707 494 001). Relative mRNA expressions were normalized to rpP2 gene expression in a two-colour duplex reaction. Primers for detection of CXXC5 (5'-tccgctgctctggagaag-3' (SEQ ID NO 4), 5'-cacacgagcagtgacattgc-3' (SEQ ID NO 5) and 6FAM-aacccaaagctgccctctcc-BBQ (SEQ ID NO 8)) and rpP2 (5'-atgcgctacgtcgcc-3'(SEQ ID NO 6), 5' -ttaatcaaaa-aggccaaatccat-3' (SEQ ID NO 7) and Cy5-agctgaatg-gaaaaaacattgaagacgtc-BBQ (SEQ ID NO 9)), were designed to be used in the same conditions of real-time PCR amplification. After initial denaturation at 95° C. for 5 min, samples were run through 44 cycles of the following conditions: denaturation for 10 seconds at 95° C. and elongation at 55° C. for 20 seconds.

Analysis of CXXC5 mRNA Expression in Two Microarray Datasets and Correlation Analysis with the Clinical Outcome of Breast Cancer Patients.

Two independent microarray datasets (Affymetrix GeneChip Human Genome HG-U133B), performed by Pawitan et al. (n=159 patient samples) and Miller et al. (n=251 patients samples), were downloaded from the Gene Expression Omnibus website (http://www.ncbi.nlm.nih.gov/geo/) with accession number GSE1456 and GSE3494. For each dataset, the whole raw data were normalized using RMA with the Expression Console software from Affymetrix. The CXXC5 mRNA expression was then calculated as the mean intensity of the 3 probesets targeting CXXC5 (222996_s_at, 224516_s_at and 233955_x_at). Patients were then clustered in three groups according to their CXXC5 mean intensity (high, intermediary or low CXXC5 expression) using K-Means clustering (KMC) based on Euclidean Distance. The patient groups with high or low CXXC5 mRNA (RINF) were then correlated with the clinical outcomes concerning survival that were also accessed through the Gene Expression Omnibus website. The Kaplan-Meier curves (for survival analysis) and the log-rank test were performed by using the statistical SPSS 15.0.

Detection of RINF by Antibody

The expression of RINF can also be determined by an antibody approach. Western blotting was carried out as previously described by Wu Y L, Dudognon C, Nguyen E, et al. Immunodetection of human telomerase reverse-transcriptase (hTERT) re-appraised: nucleolin and telomerase cross paths. J Cell Sci. 2006;119:2797-2806.

Customized rabbit polyclonal peptide-specific antibody against RINF was produced by Biogenes GmBH. The immunogenic peptide corresponds to amino acids 45-58 of the RINF protein. Antibody specificity was confirmed by competitive inhibition of the western-blot signal by addition of the immunogene peptide to the primary antibody solution. Briefly, blots were incubated with primary antibody against RINF (polyclonal antibody), and then with an appropriate peroxydase conjugated secondary antibody. Detection of protein was performed using a chemiluminescent detection system (Amersham Pharmacia Biotech).

Kit

For the expression studies of the above mentioned gene/protein, RINF, any method for quantitatively detecting the amplified product can be used, including, for example using any fluorescent dyes or labeled probes and standard methods.

Quantification of a sample containing an unknown number of target sequences typically is carried out with reference to a "standard curve" generated from a series of amplifications of samples containing the target sequence in a range of known amount. The standard curve is used to calculate an input copy number from the signal generated during an amplification. Thus, the unknown target sequence copy number in the sample of interest is estimated using the standard curve calculating the copy number that previously was determined to yield a signal equal to that observed. The concentration of the target sequence in the sample then is calculated from the input copy number and the sample size, which is determined prior to the reaction.

Quantitative estimates can be sensitive to variability in either the input sample size or in the reaction efficiency. The effect of inter-reaction variability of the input sample size on the calculated RINF concentration can be eliminated by using a control gene.

A control gene is selected which provides an independent measure of the amount of RNA in the sample. The calculated concentration of the RINF mRNA is adjusted based on the independent measure of the sample.

Variability in the amplification efficiency between the reactions used to generate the standard curve and the reaction used to assay the sample of interest can affect the applicability of the standard curve. Carrying out the reactions used to generate the standard curve simultaneously with the reaction used to assay the sample of interest, using the same "master mix" of amplification reagents, and, preferably, in adjacent wells in the same thermal cycler, will minimize the inter—reaction variation in efficiency. Alternatively, an in thermal standard can be used to adjust the results to account for variation in amplification efficiency.

The effect of inter—reaction variability of reaction efficiency between the reactions used to generate the standard curve and the reaction used to assay the sample of interest can be eliminated by using a sample of interest and is amplified with internal standard. The internal standard is added to reaction in a known copy number and co-amplified along with the RINF mRNA target. The signal generated from the known amount of the internal standard provides an indication of the overall reaction efficiency which can be used to adjust the estimate difference in copy number to account for the difference in reaction efficiencies.

The internal standard is a nucleotide sequence that contains the same primer binding sites present in the target such that it is amplified by the same primer pair, but is distinguishable from the target sequence either by length or, preferably, by the presence of a unique internal sequence. The internal standard is included in a known copy number amplifications of the sample of interest and is amplified with approximately the same efficiency as the target sequence. Any change in the signal generated by amplification of the internal standard relative to the signal expected from the standard curve reflects a change in the overall reaction efficiency and is used to adjust the estimate of the target sequence copy number correspondingly.

The fourth aspect of the invention relates to kits comprising useful components for practicing the present method: A useful kit can contain oligonucleotide primers and, optionally, probes specific for the targets regions of the RINF mRNA described. Other optional components of the kit include, for example, any standard products known by skilled scientist in the field for the quantitative RT-PCR amplification like, agents to catalyze the synthesis of primer extension (enzymes, buffer), the deoxynucleotide triphosphates (dNTP), internal standard nucleic acids, a reference RNA (positive control), non-amplified control nucleic acid (negative control), appropriate buffers for PCR or hybridization reactions, and instructions for carrying out the present method.

Another kit, or other component in the same kit, can contain SYBR green, oligonucleotide primers and, optionally, specific for the targets regions of the RINF. Other components of the kit include, substrate nucleotide triphosphates, internal standard, agents to catalyze the synthesis of primer extension, positive control, and negative control.

The examples of the present invention presented here are provided only for illustrative purposes and not to limit the scope of the invention.

RESULTS

The invention and the results of the experiments leading to the invention will now be further described, with reference to the following figures.

EXPERIMENTAL RESULTS

Figure 1:
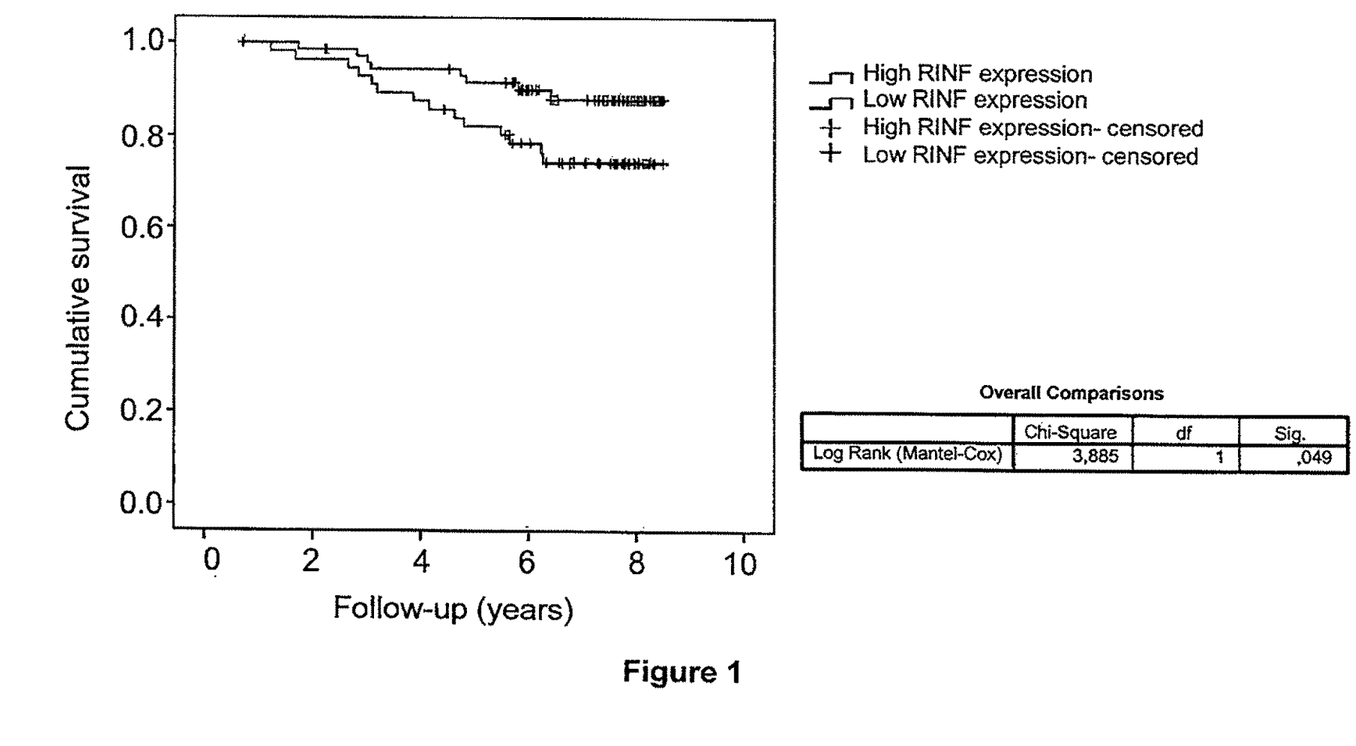
FIG. 1 shows Kaplan-Meier analysis representing cumulative survival of patients suffering from breast cancer (n=159) in which RINF mRNA expression was classified as High or Low according to the K-means clustering method (3-groups K-means clustering). The whole genome expression and survival data from the *Pawitan* et al. study, were extracted from public microarray datasets (affymetrix HG-U133B), and are accessible online at the Gene Expression Omnibus website using the accession number GSE1456. The mean intensity of the 3 probesets targeting CXXC5 mRNA expression was then correlated with the survival outcomes. The survival analysis show that a High RINF mRNA expression was associated with a poorer survival.
Figure 2:
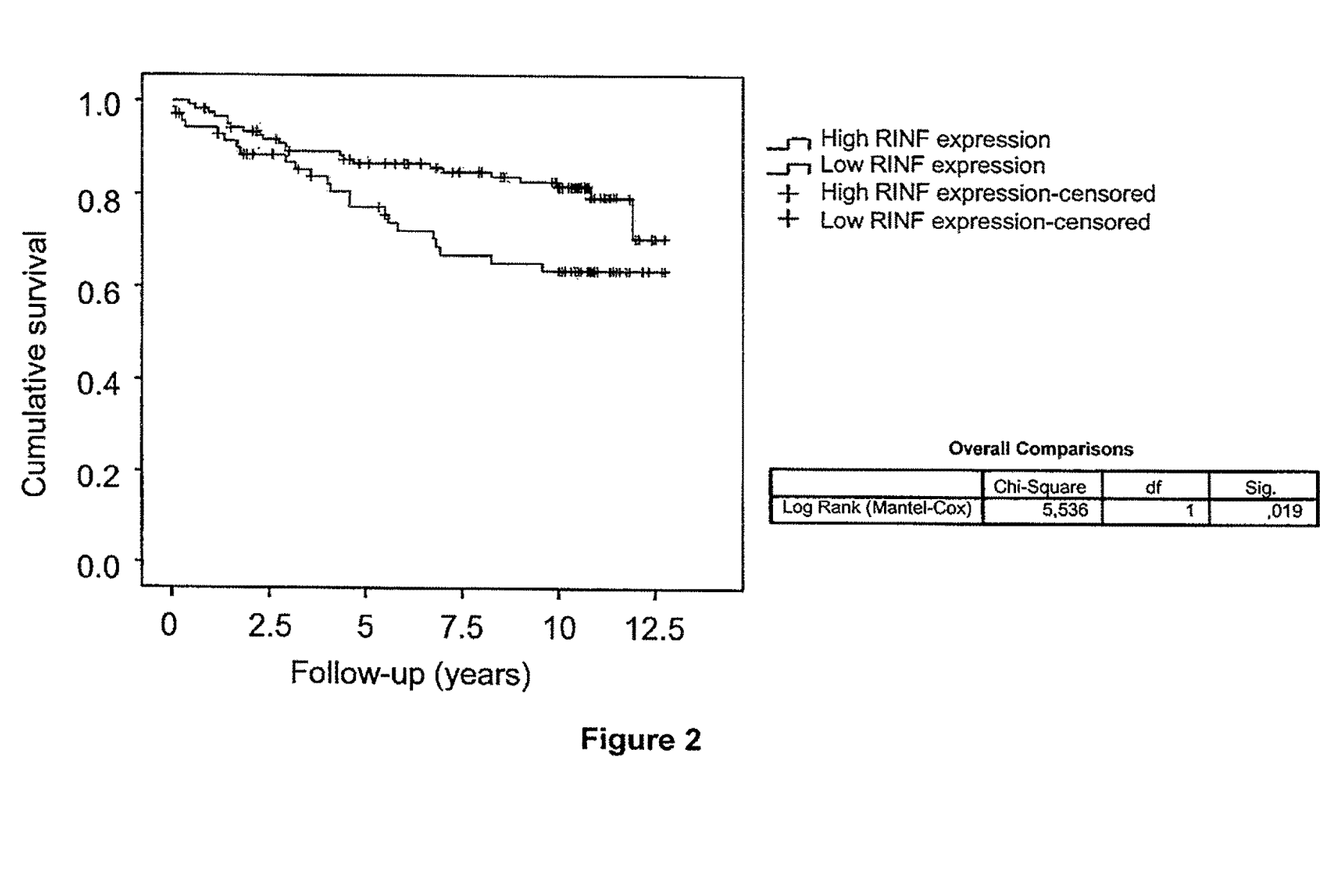
FIG. 2 shows Kaplan-Meier analysis representing cumulative survival of patients suffering from breast cancer (n=251) in which RINF mRNA expression was classified as High or Low according to the K-means clustering method (3-groups K-means clustering). The whole genome expression and survival data from the *Miller* et al. study, were extracted from public microarray datasets (affymetrix HG-U133B), and are accessible online at the Gene Expression Omnibus website using the accession number GSE3494. The mean intensity of the 3 probesets targeting CXXC5 mRNA expression was then correlated with the survival outcomes. The survival analysis show that a High RINF mRNA expression was associated with a poorer survival.

The inventors have now found that there is a correlation between the relative level of RINF expression and the prognosis for survival. These results are shown in the FIGS. 1 and 2.

Quantifying the relative mRNA level of RINF in tumors from patients with a breast cancer can help doctors determine whether or not a tumor is of good or bad prognosis, as well as if a certain treatment is likely to succeed.

Our results demonstrate that quantification of RINF mRNA expression could be a significant predictor of patient survival and cancer progression.

Indeed, by extracting the CXXC5 mRNA expression data from two independent microarray studies available in public databases, and try to correlate it with the clinical outcome, we have tested and demonstrated for the first time, a strong correlation, between a high RINF mRNA expression and low survival rate for patients suffering from breast cancer.

At the best of our knowledge, no previous study has examined the relationship between the RINF mRNA expression and a patient's prognosis in cancer. This inventive idea was tested because we have been the first to observe that this gene was deregulated in cancer cell types. However, and importantly, these results were not obvious because many genes shown to be de-regulated in cancer have no predictive value toward a patient survival or response to therapy. This is an important area of research in cancer because there are little data to help physicians chose which treatment is best for which patients or to determine when a change in treatment is warranted.

The RINF mRNA level can be measured in the tumor, or tumor biopsy, taken out at the time of surgery by using the kit and methods according to the present invention.

Potentially, this tool could be useful in the clinic for clinicians to take their decisions about whether a treatment is helping. Our ultimate goal is to continue effective treatment, but spare patients the side effects of a treatment that is destined to fail.

We also note that over-expression of RINF is not significantly linked to a poorer survival rate in melanoma so this is not a correlation that can be expected from a simply de-regulated level of RINF. Furthermore, The over-expression of CXXC5 in malignant may seem somewhat contradictory to what has previously been found in AML, where reduced expression is linked to the malignant phenotype.

Altogether, the idea that RINF mRNA expression is a prognosis factor is completely novel and non-obvious and has never been shown or described previously.

The invention claimed is:

1. A method for determining a prognosis for survival for a patient with breast cancer, comprising:
   (a) measuring the level of CXXC5 expression in a biological sample from said patient, wherein said biological sample is a tumor, or a tumor biopsy or neoplastic cell containing sample, and wherein said measuring step is performed by
      i) obtaining total RNA from the biological sample,
      ii) synthesizing first strand cDNA using the total RNA,
      iii) performing quantitative PCR of the first strand cDNA using
         a) primers specific for amplifying first strand cDNA made from CXXC5mRNA, wherein the primers are 5'-tccgctgctctggagaag-3'(SEQ ID NO: 4) and 5'cacacgagcagtgacattgc-3' (SEQ ID NO: 5) and
         b) a fluorescently labeled probe specific for detecting amplified first strand cDNA made from CXXC5 mRNA, wherein the fluorescently labeled probe is 6-FAM-aacccaaagctgccctctcc-BBQ (SEQ ID NO: 8), and
      iv) quantifying the level of CXXC5 mRNA expression in the biological sample by detecting fluorescence from the fluorescently labeled probe;
   (b) comparing the level of CXXC5 expression in said sample to a reference level of CXXC5, and
   (c) determining that said patient has an increased likelihood of survival if the level of CXXC5 expression is lower than the reference level or determining that said patient has a decreased likelihood of survival if the level of CXXC5 expression is higher than the reference level.

2. The method of claim 1, wherein the step of performing quantitative PCR is performed by
   denaturation at 95° C. for 5 min, and
   running 44 cycles of denaturation for 10 seconds at 95° and elongation at 55° C. for 20 seconds.

3. The method of claim 1, wherein the level of CXXC5 expression is normalized relative to a level of Ribosomal Protein Lateral Stalk Subunit P2 (RPLP2)expression, wherein the level of RPLP2 expression is measured by performing the quantitative PCR using a two-color duplex reaction in which the level of RPLP2 expression is measured by
  i) performing quantitative PCR of the first strand cDNA using
    a) primers specific for amplifying first strand cDNA made from RPLP2 mRNA, wherein the primers are 5'-atgcgctacgtcgcc-3'(SEQ ID NO: 6) and 5'-ttaat-caaaaaggccaaatcccat-3' (SEQ ID NO: 7), and
    b) a fluorescently labeled probe specific for detecting amplified first strand cDNA made from RPLP2 mRNA, wherein the fluorescently labeled probe is Cy5-agctgaatggaaaaaacattgaagacgtc-BBQ (SEQ ID NO: 9), and
  ii) quantifying the level of RPLP2 mRNA expression by detecting fluorescence from the fluorescently labeled probe.

4. The method of claim 1, further comprising a step of determining the efficiency of the step of performing quantitative PCR by co-amplifying a known amount of an internal standard,
  wherein the internal standard is a nucleotide sequence that contains primer binding sites present in CXXC5 first strand cDNA such that the internal standard is amplified by primers specific for amplifying first strand cDNA made from CXXC5 mRNA, but wherein the internal standard is distinguishable from the first strand cDNA made from CXXC5 mRNA by length or by containing a unique internal sequence, and if a change in the signal generated by amplification of the internal standard relative to a signal expected from a standard curve, then adjusting the level of CXXC5 expression correspondingly.

5. A method for monitoring the effectiveness of a course of treatment for a patient with breast cancer, comprising:
  A) determining, in a neoplastic cell containing biological sample obtained from the patient before treatment, a level of CXXC5 expression prior to treatment,
  B) determining, in a neoplastic cell containing biological sample obtained from the patient after treatment, the level of CXXC5 expression after treatment,
  wherein determining steps A and B are performed by
    i) obtaining total RNA from the biological sample,
    ii) synthesizing first strand cDNA using the total RNA,
    iii) performing quantitative PCR of the first strand cDNA using
      a) primers specific for amplifying first strand cDNA made from CXXC5 mRNA, wherein the primers are 5'-tccgctgctctggagaag-3'(SEQ ID NO: 4) and 5'cacacgagcagtgacattgc-3'(SEQ ID NO: 5) and
      b) a fluorescently labeled probe specific for detecting amplified first strand cDNA made from CXXC5 mRNA, wherein the fluorescently labeled probe is 6-FAM-aacccaaagctgccctctcc-BBQ (SEQ ID NO: 8), and
    iv) quantifying the level of CXXC5 mRNA expression in the biological sample by detecting fluorescence from the fluorescently labeled probe;
  C) comparing the level of CXXC5 expression before treatment with the level of CXXC5 expression after treatment, and if the level of CXXC5 expression is not decreased after treatment, then
  D) changing the treatment.

6. The method of claim 5, wherein the step of performing quantitative PCR is performed by
  denaturation at 95° C. for 5 min, and
  running 44 cycles of denaturation for 10 seconds at 95° and elongation at 55° C. for 20 seconds.

7. The method of claim 5, wherein the level of CXXC5 expression is normalized relative to a level of RPLP2 expression, wherein the level of RPLP2 expression is measured by performing the quantitative PCR using a two-color duplex reaction in which the level of RPLP2 expression is measured by
  i) performing quantitative PCR of the first strand cDNA using
    a) primers specific for amplifying first strand cDNA made from RPLP2 mRNA, wherein the primers are 5'-atgcgctacgtcgcc-3'(SEQ ID NO: 6) and 5'-ttaat-caaaaaggccaaatcccat-3'(SEQ ID NO: 7), and
    b) a fluorescently labeled probe specific for detecting amplified first strand cDNA made from RPLP2 mRNA, wherein the fluorescently labeled probe is Cy5-agctgaatggaaaaaacattgaagacgtc-BBQ (SEQ ID NO: 9), and
  ii) quantifying the level of RPLP2 mRNA expression by detecting fluorescence from the fluorescently labeled probe.

8. The method of claim 5, further comprising a step of determining the efficiency of the step of performing quantitative PCR by co-amplifying a known amount of an internal standard,
  wherein the internal standard is a nucleotide sequence that contains primer binding sites present in CXXC5 first strand cDNA such that the internal standard is amplified by primers specific for amplifying first strand cDNA made from CXXC5 mRNA, but wherein the internal standard is distinguishable from the first strand cDNA made from CXXC5 mRNA by length or by containing a unique internal sequence, and if a change in the signal generated by amplification of the internal standard relative to a signal expected from a standard curve, then adjusting the level of CXXC5 expression correspondingly.

9. A method for treating a patient with breast cancer, said method comprising:
  (a) measuring the level of CXXC5 expression in a biological sample from said patient, wherein said biological sample is a tumor, or a tumor biopsy or a neoplastic cell containing sample; wherein measuring step (a) performed by
    i) obtaining total RNA from the biological sample,
    ii) synthesizing first strand cDNA using the total RNA,
    iii) performing quantitative PCR of the first strand cDNA using
      a) primers specific for amplifying first strand cDNA made from CXXC5 mRNA, wherein the primers are 5'-tccgctgctctggagaag-3'(SEQ ID NO: 4) and 5'cacacgagcagtgacattgc-3'(SEQ ID NO: 5) and
      b) a fluorescently labeled probe specific for detecting amplified first strand cDNA made from CXXC5 mRNA, wherein the fluorescently labeled probe is 6-FAM-aacccaaagctgccctctcc-BBQ (SEQ ID NO: 8), and
    iv) quantifying the level of CXXC5 mRNA expression in the biological sample by detecting fluorescence from the fluorescently labeled probe;
  (b) comparing the level of CXXC5 expression in said sample to a reference level of CXXC5 from normal breast tissue controls;

(c) classifying said patient as belonging to either a group having an increased likelihood of survival if the level of CXXC5 expression is lower than the reference level or a group having a decreased likelihood of survival if the level of CXXC5 expression is higher than the reference level; and (d) based on said classifying step, administering to the patient a suitable course of treatment that is likely to successfully treat the breast cancer.

10. The method of claim 9, wherein the step of performing quantitative PCR is performed by
denaturation at 95° C. for 5 min, and
running 44 cycles of denaturation for 10 seconds at 95° and elongation at 55° C. for 20 seconds.

11. The method of claim 9, wherein the level of CXXC5 expression is normalized relative to a level of RPLP2 expression, wherein the level of RPLP2 expression is measured by performing the quantitative PCR using a two-color duplex reaction in which the level of RPLP2 expression is measured by
i) performing quantitative PCR of the first strand cDNA using
a) primers specific for amplifying first strand cDNA made from RPLP2 mRNA, wherein the primers are 5'-atgcgctacgtcgcc-3'(SEQ ID NO: 6) and 5'-ttaatcaaaaaggccaaatcccat-3'(SEQ ID NO: 7), and
b) a fluorescently labeled probe specific for detecting amplified first strand cDNA made from RPLP2 mRNA, wherein the fluorescently labeled probe is Cy5-agctgaatggaaaaaacattgaagacgtc-BBQ (SEQ ID NO: 9), and
ii) quantifying the level of RPLP2 mRNA expression by detecting fluorescence from the fluorescently labeled probe.

12. The method of claim 9, further comprising a step of determining the efficiency of the step of performing quantitative PCR by co-amplifying a known amount of an internal standard,
wherein the internal standard is a nucleotide sequence that contains primer binding sites present in CXXC5 first strand cDNA such that the internal standard is amplified by primers specific for amplifying first strand cDNA made from CXXC5 mRNA, but wherein the internal standard is distinguishable from the first strand cDNA made from CXXC5 mRNA by length or by containing a unique internal sequence, and if a change in the signal generated by amplification of the internal standard relative to a signal expected from a standard curve, then adjusting the level of CXXC5 expression correspondingly.

13. A method of measuring a level of CXXC5 expression in a biological sample that is a tumor, a tumor biopsy or a neoplastic cell containing sample from a patient with breast cancer, comprising
i) obtaining total RNA from the biological sample,
ii) synthesizing first strand cDNA using the total RNA,
iii) performing quantitative PCR of the first strand cDNA using
a) primers specific for amplifying first strand cDNA made from CXXC5 mRNA, wherein the primers are 5'-tccgctgctctggagaag-3'(SEQ ID NO: 4) and 5' cacacgagcagtgacattgc-3'(SEQ ID NO: 5) and
b) a fluorescently labeled probe specific for detecting amplified first strand cDNA made from CXXC5 mRNA, wherein the fluorescently labeled probe is 6-FAM-aacccaaagctgccctctcc-BBQ (SEQ ID NO: 8), and
iv) quantifying the level of CXXC5 mRNA expression in the biological sample by detecting fluorescence from the fluorescently labeled probe.

14. The method of claim 13, wherein the method is used to prognose survival for a patient with breast cancer by
comparing the level of CXXC5 expression in the biological sample to a reference level of CXXC5 from normal breast tissue controls; and
determining that the patient has an increased likelihood of survival if the level of CXXC5 expression is lower than the reference level, or determining that said patient has a decreased likelihood of survival if the level of CXXC5 expression is higher than the reference level.

* * * * *